(12) United States Patent
Greenberg

(10) Patent No.: US 6,827,735 B2
(45) Date of Patent: Dec. 7, 2004

(54) ENDOVASCULAR DEVICE HAVING A STENT

(75) Inventor: Roy K. Greenberg, Mayfield, OH (US)

(73) Assignee: Cook Incorporated, Bloomington, IN (US)

(*) Notice: Subject to any disclaimer, the term of this patent is extended or adjusted under 35 U.S.C. 154(b) by 206 days.

(21) Appl. No.: 09/798,489

(22) Filed: Mar. 2, 2001

(65) Prior Publication Data

US 2001/0027338 A1 Oct. 4, 2001

Related U.S. Application Data

(60) Provisional application No. 60/186,586, filed on Mar. 3, 2000.

(51) Int. Cl.[7] .................................................. A61F 2/06
(52) U.S. Cl. ..................................................... 623/1.25
(58) Field of Search ............................... 623/1.13, 1.15, 623/1.16, 1.23, 1.25, 1.27, 1.36, 1.21, 1.35; 606/191, 194, 192, 195, 198, 200, 157, 158

(56) References Cited

U.S. PATENT DOCUMENTS

| | | | |
|---|---|---|---|
| 4,183,102 A | * | 1/1980 | Guiset ........................ 623/1.25 |
| 4,580,568 A | | 4/1986 | Gianturco |
| 5,015,253 A | | 5/1991 | MacGregor |
| 5,035,706 A | | 7/1991 | Giantureo et al. |
| 5,197,978 A | | 3/1993 | Hess |
| 5,330,528 A | * | 7/1994 | Lazim ........................ 623/1.25 |
| 5,415,664 A | | 5/1995 | Pinchuk |
| 5,562,728 A | | 10/1996 | Lazarus et al. |
| 5,607,468 A | * | 3/1997 | Rogers et al. ............. 623/1.15 |
| 5,609,628 A | * | 3/1997 | Keranen .................... 623/1.36 |
| 5,639,278 A | | 6/1997 | Dereume et al. |
| 5,643,208 A | * | 7/1997 | Parodi ..................... 604/96.01 |
| 5,693,088 A | * | 12/1997 | Lazarus ...................... 606/195 |
| 5,718,724 A | | 2/1998 | Goicoechea et al. |
| 5,824,040 A | | 10/1998 | Cox et al. |
| 5,976,179 A | * | 11/1999 | Inoue .......................... 606/194 |
| 6,007,575 A | * | 12/1999 | Samuels ..................... 606/195 |
| 6,013,190 A | | 1/2000 | Berg et al. |
| 6,030,414 A | | 2/2000 | Taheri |
| 6,210,429 B1 | | 4/2001 | Vardi et al. |
| 6,312,462 B1 | * | 11/2001 | McDermott et al. ....... 623/1.25 |
| 6,395,019 B2 | * | 5/2002 | Chobotov .................. 623/1.36 |

FOREIGN PATENT DOCUMENTS

| | | |
|---|---|---|
| DE | 93192673 | 4/1994 |
| EP | 0686379 | 12/1995 |
| EP | 0722701 | 7/1996 |
| EP | 0765643 | 4/1997 |
| WO | 9513033 | 5/1995 |
| WO | 9709008 | 3/1997 |
| WO | 9729716 | 8/1997 |
| WO | 9844873 | 10/1998 |
| WO | 9853761 | 12/1998 |
| WO | 9939662 | 8/1999 |

\* cited by examiner

*Primary Examiner*—David O. Reip
*Assistant Examiner*—Jessica R. Baxter
(74) *Attorney, Agent, or Firm*—Richard J. Godlewski

(57) ABSTRACT

A stent (10,20,30,40,50,58,60,80,90,100,150,254,256,300) having an inflatable member or a plurality of members affixed directly thereto. One type of inflatable member, or pair or plurality of members, may be affixed to the outer stent surface to expand upon inflation to seal against the vessel wall, and optionally to each other as well, and may be annular (14,18,20,42,46,82,94) or spirally (22,24,26,84) or asymmetrically (32,34,36) configured. In another embodiment a member (304), or pair of opposed members (306), can be affixed to the inner stent surface and used to occlude the lumen upon inflation. The device of the present invention can also be utilized with conventional stent grafts (152) to protect branch vessels that are involved in the aneurysm span.

11 Claims, 6 Drawing Sheets

ENDOVASCULAR DEVICE HAVING A STENT

RELATED APPLICATION INFORMATION

This application claims priority from U.S. Provisional Patent Application Ser. No. 60/186,586 filed Mar. 3, 2000.

FIELD OF THE INVENTION

This relates to the field of medical devices and more particularly to endovascular devices having a stent.

BACKGROUND OF THE INVENTION

In recent years treatment of aneurysms has included the use of stent grafts that are emplaced within the vascular networks, and include one or more stents affixed to graft material. The stent grafts are secured at a treatment site by endovascular insertion utilizing introducers and catheters, whereafter they are enlarged radially and remain in place by self-attachment to the vessel wall. In particular, stent grafts are known for use in treating descending thoracic and abdominal aortic aneurysms where the stent graft at one end defines a single lumen for placement within the aorta and at the other end is bifurcated to define two lumens, for extending into the branch arteries.

One example of such a stent graft is PCT Publication No. WO 98/53761 in which the stent graft includes a sleeve or tube of biocompatible graft material (such as Dacron or polytetrafluoroethylene) defining a lumen and several stents secured therealong, with the stent graft spanning the aneurysm extending along the aorta proximally from the two iliac arteries, and the reference also discloses the manner of deploying the stent graft in the patient utilizing an introducer assembly. The graft material-covered portion of the single-lumen proximal end of the stent graft bears against the wall of the aorta above the aneurysm to seal the aneurysm at a location that is distal of the entrances to the renal arteries. Thin wire struts of a proximal stent extension traverse the entrances without occluding them while securing the stent graft in position within the aorta when the stent self-expands, since no graft material is utilized along the proximal stent; an extension is affixed to one of the legs of the stent graft to extend along a respective iliac artery, and optionally extensions may be affixed to both legs. Another known stent graft is the Zenith AAA stent graft sold by Cook Incorporated, Bloomington, Ind.

Stent grafts are also known in which an inflatable balloon is positioned within the collapsed stent graft before and during placement of the stent graft in a patient using an introducer assembly; the balloon is then expanded to increase the diameters of the several stents and the graft material until the stent graft bears against the vessel wall at least at its distal and proximal ends. Such stent grafts are disclosed in U.S. Pat. Nos. 5,639,278; 5,562,728 and 5,718,724. In U.S. Pat. No. 5,330,528, a plurality of expandible chambers is disclosed, with several supply pipes extending to respective chambers for inflation thereof.

Use of such stent grafts requires that the graft not close off or occlude or obstruct entrances to other branch arteries, such as the renal arteries. Placement of the single-lumen or proximal end of the stent graft, at least the portion having graft material, must be located spaced axially from branch arteries and toward the aneurysm neck.

It is desired to provide an endovascular device that is useful for aneurysms that span the branch arteries, or that have intrarenal necks of minimal length.

SUMMARY OF THE INVENTION

In accordance with the present invention, an endovascular device includes at least one stent and at least one inflatable portion or member which is affixed to the stent, with the stent generally having no graft material thereon.

In one embodiment, the inflatable portion is disposed about a lumen of the device to define a cuff and is utilized either to expand a stent or to define a seal externally to a stent or to a stent graft, and both may be found on a particular device of the present invention. The inflatable portion may be so oriented as to be annular, or may be spiral, or may be asymmetric in its inflated state. If a device includes more than one inflatable portion, each such portion may be inflatable by a dedicated discrete lumen, or a single lumen with multiple branches to the respective inflatable portions.

In another embodiment, the device of the present invention may be used with a stent graft and extend radially outwardly therefrom to enter a branch vessel. In one particular application where the stent graft is to be emplaced for treating an abdominal aortic aneurysm, the device of the present invention would be affixable to the stent graft remote from the iliac legs thereof for placement at a proximal neck of the aneurysm, to enter one of the renal arteries and to define a lumen in communication with the stent graft lumen. The stent of the device would be expanded within the proximal portion of the renal artery. A plurality of such devices could be utilized with the stent graft for maintaining the patency of numerous branch arteries.

In another aspect, the device of the present invention could be utilized to extend from the single-lumen end of a stent graft that otherwise would terminate only just adjacent to a branch artery; the device could be used for aneurysms having proximal necks of minimal length at the renal artery entrances, where conventional stent grafts could not generally be used. The stent of the device would comprise a plurality of spaced struts or legs and would traverse the branch artery entrance without occluding it since no graft material would be utilized on the stent, allowing blood perfusion through openings between the stent struts or legs. An inflatable portion of the device would surround the end portion of the stent graft and be inflatable to become pressed against the vessel wall, thereby sealing the aneurysm.

In a further embodiment, a device of the present invention could comprise an elongate main stent either without graft material or with graft material at both the distal and proximal end portions. Additional stents could extend radially outwardly from the main stent for placement within branch vessels, each with one or more inflatable portions, and each defining a lumen in communication with the lumen of the main stent such as through openings between struts of the main stent.

Another embodiment of the stent/balloon of the present invention could include a plurality of members affixed along the outer stent surface that are spaced apart when deflated providing spacings for instrumentation to extend therebetween and outwardly from the stent, but which press against each other and the vessel wall to seal about the stent when inflated.

An additional embodiment provides an occlusion device wherein, for example, a pair of opposed inflatable portions are affixed to the inner surface of the stent such that upon inflation they press against each other and traverse the lumen of the stent.

In additional aspects, the device of the present invention could utilize stents with a pattern of spiral struts, or with a series of stent segments. A stent may be utilized that includes struts at one end that are expandable to rotate radially outwardly until in engagement with the wall of the aorta about the periphery of a branch vessel, for securing the placement of the device with respect to the branch artery.

The present invention also includes a method comprising the steps of deploying a stent and an inflatable member at a deployment site within a vessel of a patient, and inflating the inflatable member to abut the vessel wall and define a seal between the stent and the vessel wall.

Embodiments of the present invention will now be described by way of example with reference to the accompanying drawings.

BRIEF DESCRIPTION OF THE DRAWINGS

FIG. 14 is an isometric view of the device of the present invention utilized with an elongate stent graft for an aneurysm that extends past the renal arteries, with devices of the present invention extending radially outwardly from the stent graft to enter the branch arteries to maintain the patency thereof, while the elongate stent graft proximal end is secured to the vessel wall above the branch arteries;

DETAILED DESCRIPTION

Figure 1:
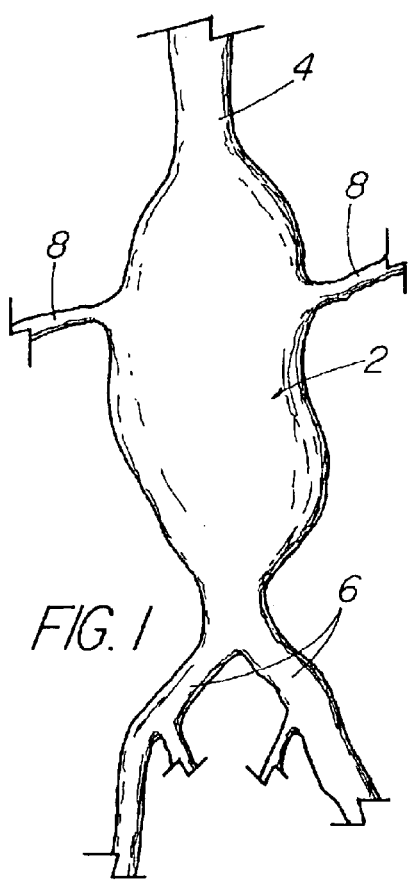
FIG. 1 is a longitudinal section view of an aneurysm of the aorta adjacent to the iliac arteries and showing the renal arteries.

In FIG. 1 is illustrated an aneurysm 2 of the aorta 4 in the abdomen of a patient proximal to the iliac arteries 6, with the renal arteries 8 spaced proximally thereof. Stent grafts presently known, such as that disclosed in PCT Publication No. WO 98/53761, could not generally be utilized at least alone to treat such an aneurysm 2 since the wall of the stent graft main lumen formed by graft material would traverse the branch arteries thereby occluding flow, as the proximal end of the stent graft would have to be secured to healthy vessel wall spaced from the aneurysm to thereby seal off the aneurysm proximally, with the legs of the stent graft being secured to the iliac artery walls below the aneurysm, to seal the aneurysm distally.

Figure 2:
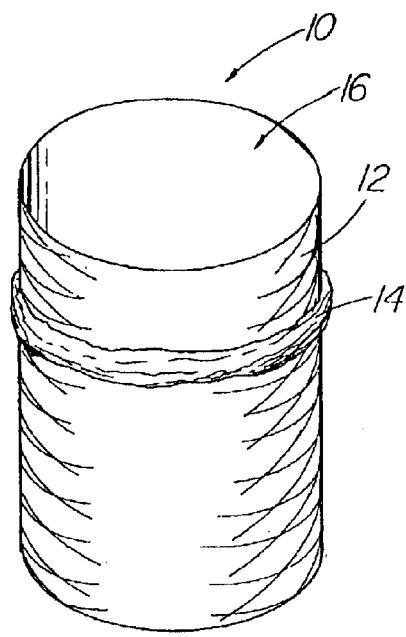
FIGS. 2 and 3 are isometric views of first and second embodiments of the present invention having a stent and a single annular inflatable band or multiple annular bands.

The endovascular device 10 of the present invention, as shown in FIG. 2, includes at least one stent 12 and at least one inflatable portion 14, with a lumen 16 extending axially therethrough. In most Figures, the stent frame structure is depicted generally as a grid having struts that are oriented at an angle with respect to the longitudinal axis of the lumen, and the inflatable portions may be affixed to surfaces of the grid such as by adhesive bonding.

Figure 3:
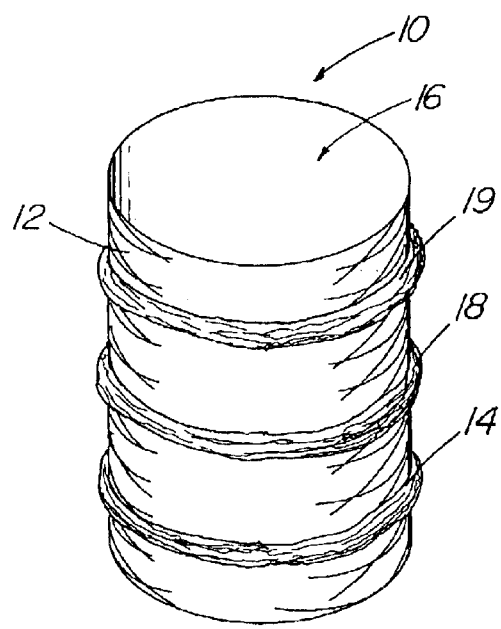
Figure 11:
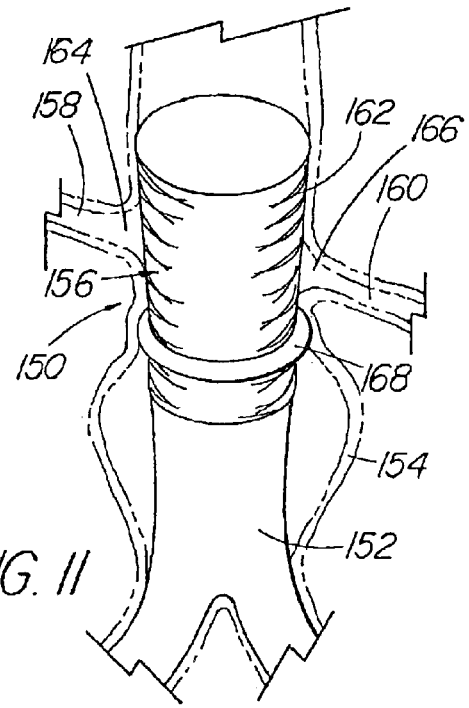
FIG. 11 is an isometric view illustrating an embodiment of the present invention in situ in the aorta extending from an end of an abdominal aortic stent graft proximally past entrances to opposed renal arteries, and having an inflatable portion sealing against the vessel wall to seal the aneurysm.

In FIG. 3, device 10 utilizes second and third annular inflatable portions 18, 19 in addition to first inflatable portion 14. With this device, the first and second inflatable portions 14, 18 could expand the stent 10, while the third inflatable portion 19 could be a sealing balloon that surrounds the stent and expand to form a seal against the wall of the aorta surrounding the periphery to the entrance to a branch artery (as illustrated in FIG. 11). The several inflatable portions may have separate discrete inflation lumens (see FIG. 13).

Figure 4A:
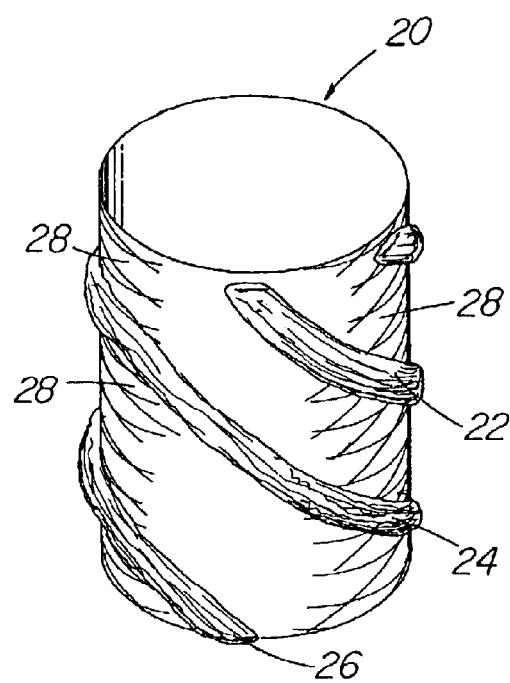
FIGS. 4A and 4B are isometric views of a third embodiment before and after balloon inflation, where the balloons have a nonannular pattern such as spiral.
Figure 4B:
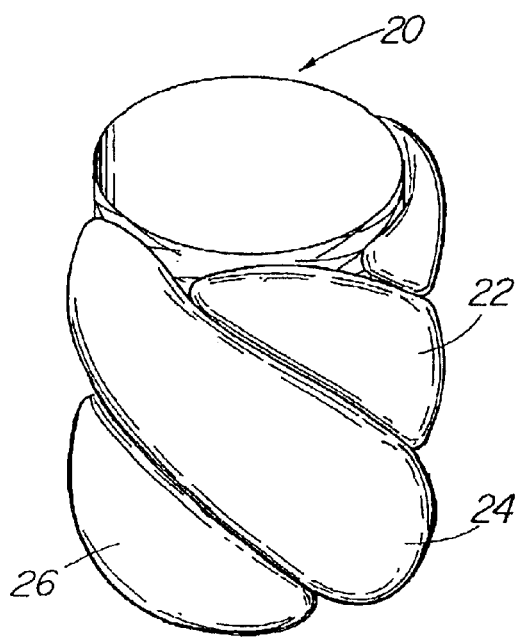

The device 20 of FIG. 4A includes several inflatable portions or members or balloons 22,24,26 that extend in spiral fashion about the stent outer surface spaced apart when not inflated, which would allow instrumentation to extend through and between the struts of the stent and spacings 28 between the deflated members. In FIG. 4B, the members are shown inflated as they would be within a vessel to press against the vessel walls, and would also press against each other to define a seal between the stent and the vessel wall.

Figure 5:
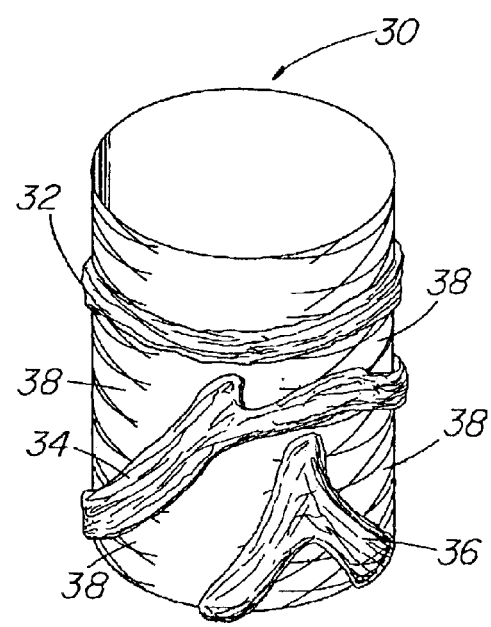
FIG. 5 is similar to FIGS. 4A and 4B of a fourth embodiment where the balloons have an asymmetric pattern.

In FIG. 5, several inflatable members or balloons 32,34,36 of device are shown in an asymmetric pattern selected to complement certain vasculatory anatomy such that spaces are defined between the balloons when they are deflated but which can seal against the vessel wall and each other after inflation except in the larger spacings 38 between balloons that may align with branch vessel entrances to permit blood flow thereinto.

Figure 6:
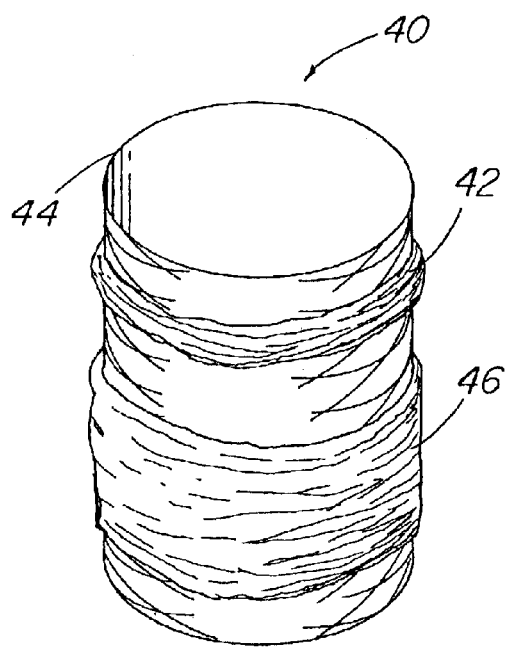
FIG. 6 is a fifth embodiment of the present invention having a first annular inflatable portion at one end to seal outwardly against the vessel wall, and a second annular inflatable portion proximate the other end that would expand to fill the aneurysm sac.
Figure 8:
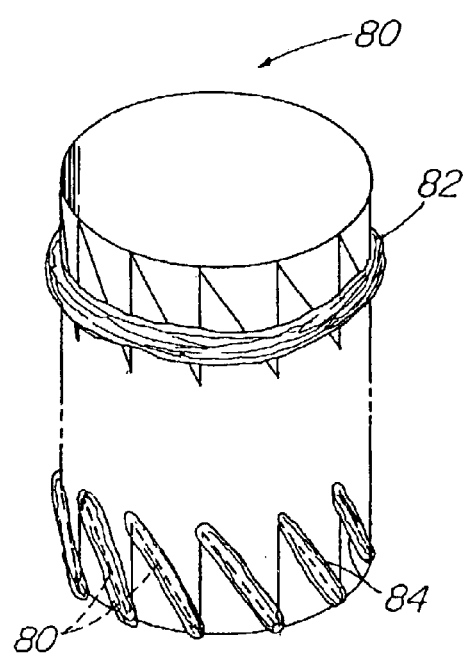
FIGS. 7 and 8 are sixth and seventh embodiments of the present invention having a Z-type stent or a spiral stent, respectively, and multiple branches with stent balloons.

Device 40 of FIG. 6 includes a first inflatable portion 42 at a first end of stent graft 44, to establish a seal against healthy vessel wall adjacent the entrance to an aneurysm. A second inflatable portion 46 is larger, preferably thin-walled, for filling the aneurysm sac upon inflation thereof.

Figure 7:
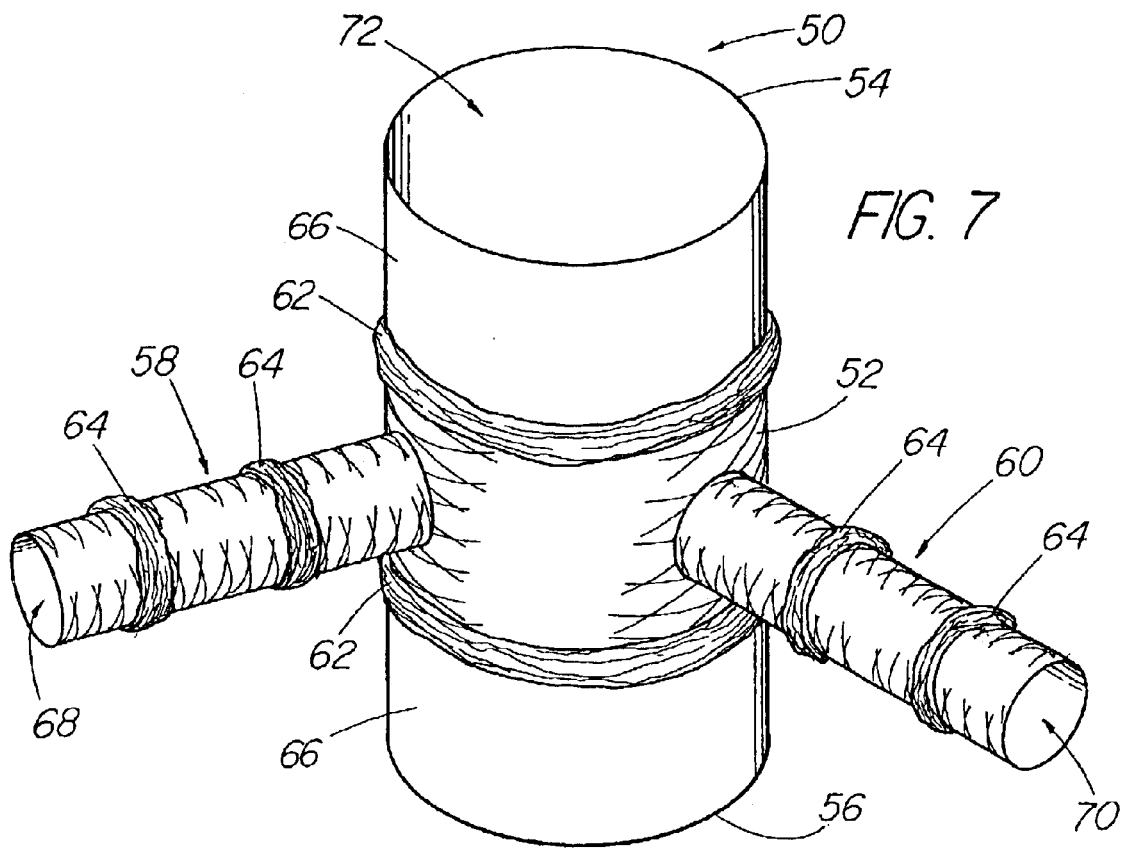
Figure 9:
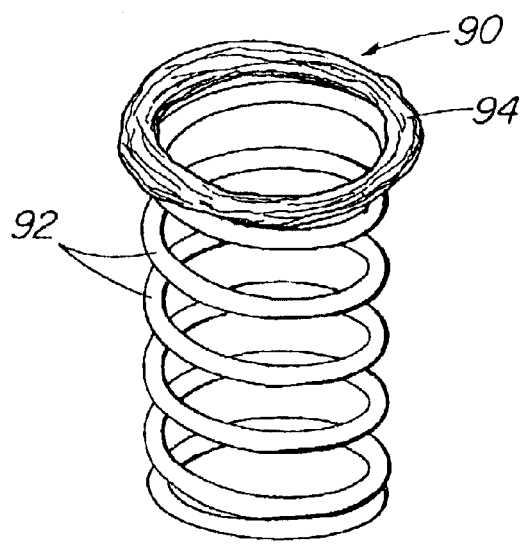
FIG. 9 is an eighth embodiment having a stent that is adapted to be secured at the entrance to a branch artery.

In FIG. 7 is illustrated another embodiment 50 of the endovascular device of the present invention. A main stent 52 includes a first end 54 and a second end 56. Second and third stents 58,60 are added in a modular fashion prior to inflation of any balloons or after selective inflations, to extend radially outwardly from main stent 52 remote from ends 54,56 to extend into and along branch arteries. Main stent 52 includes at least two inflatable portions 62 as shown, and each of second and third stents 58,60 is shown to include one or more inflatable portions 64. Graft material 66 is shown surrounding portions of main stent 52 adjacent to first and second ends 54,56; use of graft material 66 is optional, however, and may be combined with balloons. Lumens 68,70 of second and third stents 58,60 are in communication with central lumen 72 of main stent 52. Second and third stents 58,60 would extend outwardly from main stent 52 through openings between the struts thereof. Second and third stents 58,60 would provide a mechanism to preserve flow into branch vessels through the use of external balloons to seal the vessels off from the aneurysmal sac.

Figure 7A:
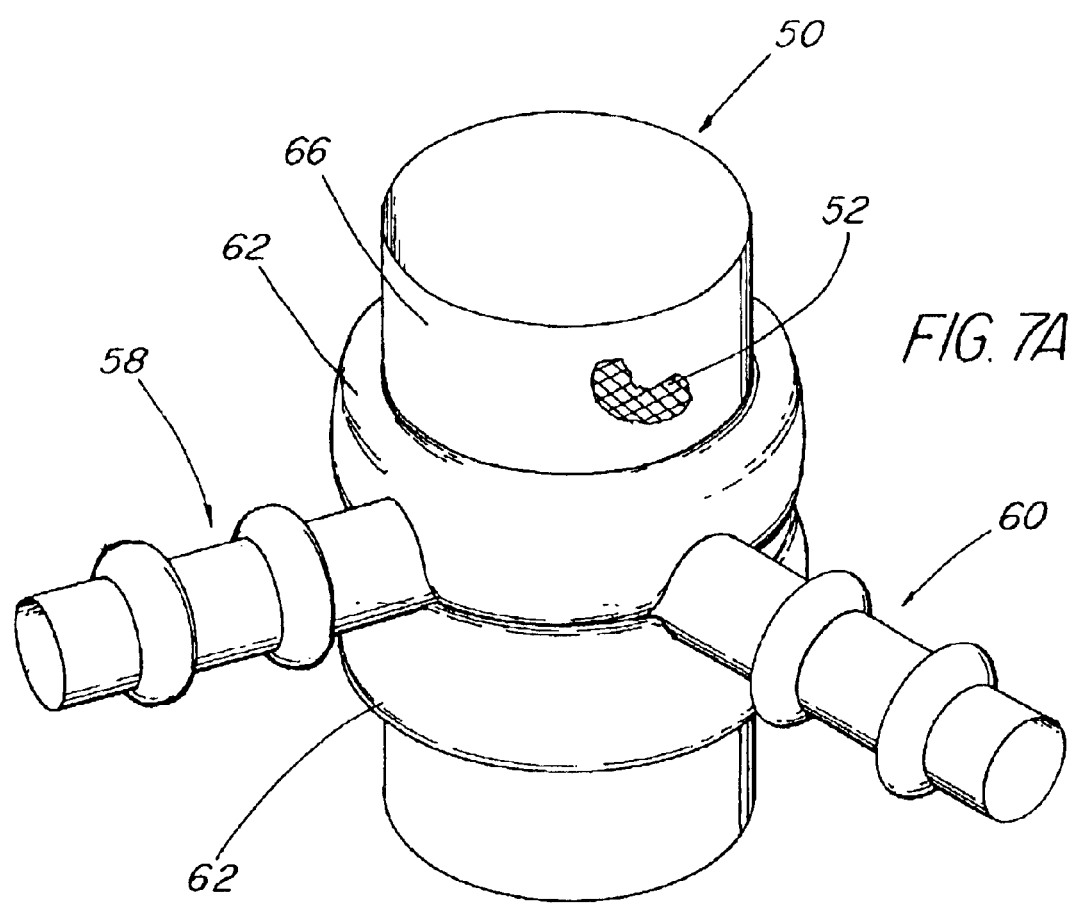
FIG. 7A is the sixth embodiment of the present invention of FIG. 7 with the Z-type stent with stent balloons inflated such chat the inflated balloons press against the multiple branches extending radially outwardly through the scent end the inflated balloons.

FIG. 7A depicts embodiment 50 of the endovascular device of the present invention of FIG. 7 with at least two inflatable portions 62 inflated. Medical devices such as second and third scents 58, 60 extend outwardly through main stent 52 and between the at least two inflated members or portions 62. As shown, the at least two inflated members or portions 62 press against second and third stents 58, 60.

Figure 10:
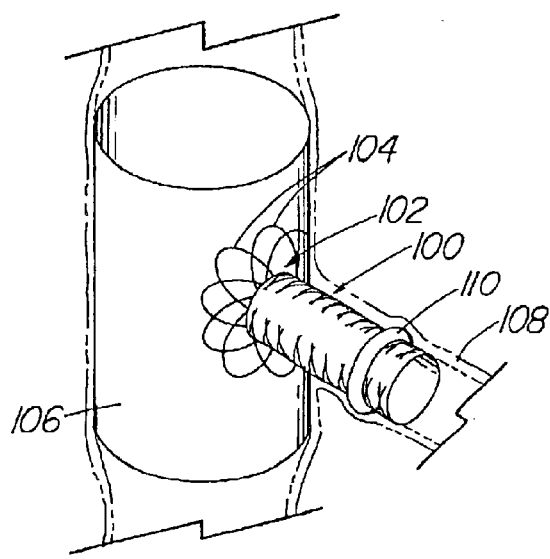
FIG. 10 is a ninth embodiment illustrating a main stent with two branch stents extending radially outwardly therefrom, each having two annular inflatable portions, with the main stent also having two annular inflatable portions positioned on either side of the pair of branch stents.

In FIG. 10, stent 100 is a button stent that has a greater expansile capacity at proximal end 102 with strut portions 104 that are expandable to deflect radially outwardly and rotate backwardly to become engaged with the vessel wall or with struts of another stent 106 surrounding the periphery of the entrance of a branch artery 108 to prevent movement of the stent into the branch artery 108; the inflatable portion 110 seals the branch artery from the aneurysm in which stent 106 is affixed to provide a sealing mechanism so that a stent assembly may be defined for multiple "branches". Strut portions 104 preferably are of the type to self expand upon release from within a retractable sheath (not shown) but may be balloon expandable and shapable by altering the balloon shape and expansion/inflation characteristics.

Figure 12:
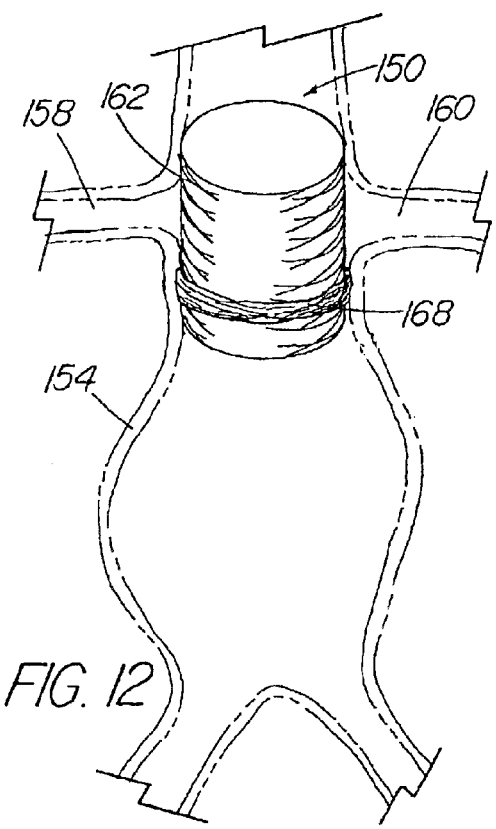
Figure 13:
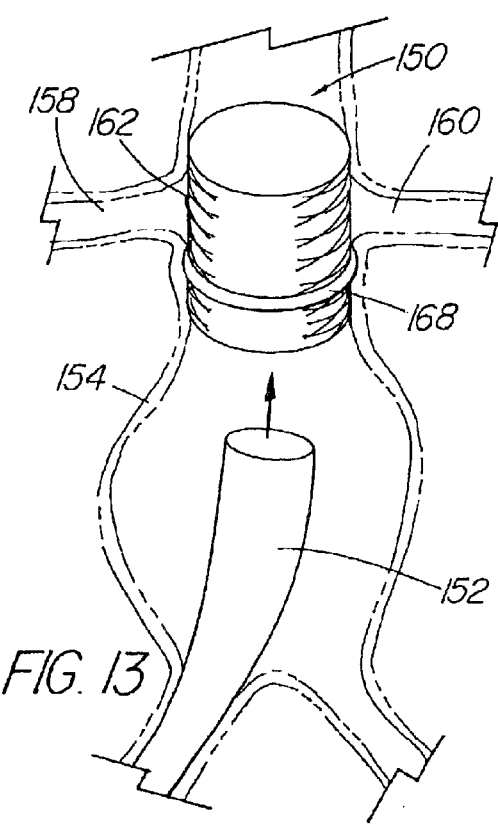
FIGS. 13 and 14 illustrate the placement of the proximal neck device of FIG. 11, with the device initially placed at a minimal-sized infrarenal neck, and subsequently inflated in FIG. 12 to approximate an extended proximal aneurysm neck to facilitate placement of the abdominal aortic stent graft.

FIGS. 11 to 13 depict placement of an endovascular device of the present invention in situ within an abdominal aortic aneurysm. In FIG. 11, a device 150 of the present invention is used in conjunction with an abdominal aortic stent graft 152 of conventional design, for use in treating an aneurysm 154 having an infrarenal neck 156 of minimal length adjacent to branch or renal arteries 158,160. Device 150 includes a stent 162 initially positioned (FIG. 12) to traverse the entrances 164,166 of renal arteries 158,160, with the stent being free of graft material and thereby not occluding the renal arteries. Device 150 may be of the type that is self-expandable, or is expandable by use of a stent-expanding balloon. Annular inflatable portion 168 of device 150 surrounds stent 162 and is located immediately adjacent to entrances 164,166 of renal arteries 158,160 and is shown uninflated (FIG. 12), to seal against vessel wall to close off the entrance 156 to the aneurysm 154 upon inflation. When device 150 is so placed and inflatable portion 168 has been inflated, device 150 approximates an aneurysmal neck of substantial length enabling the use of a conventional stent graft. The proximal end of the stent graft 152 is insertable into the lumen of device 150 and attachable thereto following the same procedures as if it were being attached to the vessel wall. Optionally, the device may be affixed about a distal end of the stent graft prior to placement, to simplify the procedure.

Figure 14:
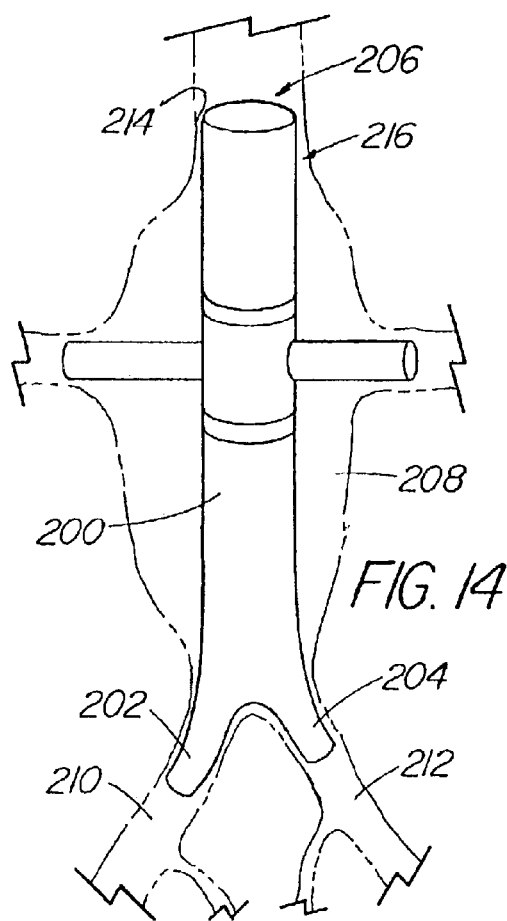

In FIG. 14, an elongate stent graft 200 extends from legs 202,204 to a proximal end 206, and positioned in and along aneurysm 208 from iliac arteries 210,212 to healthy vessel wall 214 adjacent to entrance 216. Aneurysm 208 is of the type to encompass the entrances to branch arteries, such as renal arteries or superior mesenteric arteries (SMA), which of course can not be allowed to become occluded or blocked by the stent graft.

Figure 15:
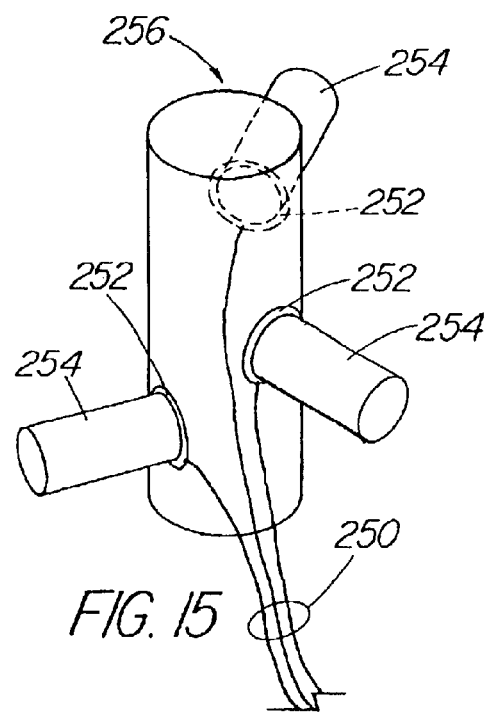
FIG. 15 is an isometric view similar to FIG. 14 with the several inflatable portions of a stent graft assembly having respective lumens for separate selective inflation thereof.

FIG. 15 demonstrates potential pre-deployment access or inflation lumens 250 for the inflatable sealing members 252 each of the branch segments 254 of a stent graft assembly 256.

Figure 16:
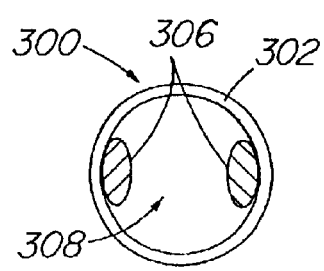
FIGS. 16 to 19 are end views of an additional embodiments of the present invention that comprise occluders.
Figure 18:
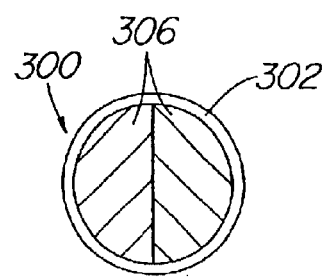
Figure 17:
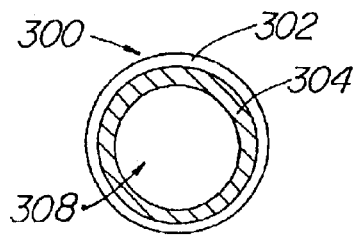
Figure 19:
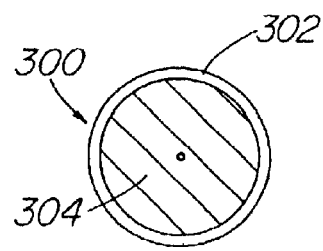

The present invention also is useful in defining a detachable occluder 300. As seen in FIGS. 16 and 17, the inflatable member is mounted along the inside of the stent 302 and is uninflated when the stent is being placed; the member may be annular 304, or may comprise opposing portions 306,306. Then, as shown in FIGS. 18 and 19, the inflatable portion(s) is (are) expanded by a diffusable solution, not only to fully expand the stent but also to completely traverse the lumen 308 of the stent and thereby completely occlude the artery. The inflatable portion(s) may be the length of the stent, and may be from 10 to 40 mm in length. After inflation, the inflation mechanism may be detached.

One stent useful with the present invention is the Z-STENT™, sold by Cook Incorporated of Bloomington, Indiana. A similar stent is disclosed in U.S. Pat. No. 4,580,568. Another stent is disclosed in U.S. Pat. No. 5,015,253 and having a spiral strut configuration.

A stent useful with the present invention could comprise stainless steel, Nitinol, titanium alloy, tantalum or Elgiloy, among others. The stents could be lined with thin-walled material that is possibly biodegradable or dissolvable to prevent balloon intrusion into the lumen of the stent. The balloons defining the inflatable portions could comprise latex, silicone rubber, PET (polyethylene terephthalate) or nylon and so forth, and could be impermeable or semipermeable. Attachment of the inflatable member to the stent may be by use of an appropriate adhesive or bonding agent. The luminal inflation mechanism could be a single lumen connected to each inflatable portion, or a plurality of discrete lumens that are separately inflatable for selective and/or sequential inflation thereof. The filling mechanism can involve a series of detachable lumens that are detached by a trigger mechanism at the delivery device level, a sheath that is advanced over the balloon lumen to separate the devices, or a pressure type valve. In addition, the lumens of the balloons can be joined, in which case all the balloons can be filled off a single lumen, or there can be discrete filling chambers with separate lumens, involving separate disconnect mechanisms.

The substance used to inflate the lumen can vary from standard saline or air, to a silicone based substance or something that will solidify over time. The mechanism of this can occur by coupling a balloon material that is selectively permeable with an inflation medium that solidifies with the diffusion of the substance to which the balloon material is permeable. This would allow the chemical constitution of the balloon contacts to vary, thus altering the physical properties over time.

Another approach would be to provide a substance within the deflated member or balloon, that expands when exposed to ultraviolet or visible light that activates a catalyst within the substance, whereby the substance foams up to inflate the inflatable member; in such a case no inflation lumen is necessary, and the light energy can be transmitted by an optical fiber within the catheter such as being secured to the wire guide.

An inflation lumen monitoring device (such as a wire or module that measures pressure) can be placed within, or just outside a balloon lumen such that when the balloon is inflated the device can register the pressure transmitted to the balloon lumen or the wall of the aneurysm/artery. The sensor will have to have a means of transmitting the data to a monitor placed on the patient in the proximity of the device or over the phone line.

as some pacemakers do.

The inflated member can either be big and bulky to fill the aneurysmal sac or, more likely, have properties to be sandwiched between stents, in such a way so that it becomes a "lining" like graft material over the lumen or outer stent scaffold upon inflation.

Additionally, an inflatable member may be utilized within the stent lumen and sufficiently affixed thereto along the inner surface when the stent is in its reduced dimension state, to be utilized for expansion of the stent upon deployment within a vessel whereafter the inflatable member may thereafter be deflated and removed.

What is claimed is:

1. An intravascular medical device, comprising:
    a stent having a lumen therethrough and having a small dimension for placement into a delivery device for delivery to a deployment site in a vessel of a patient and being expandible thereat to an enlarged dimension, and
    a plurality of inflatable members secured to said stent and being sufficiently small in a deflated state to be placed into said delivery device for delivery to said deployment site,
    said plurality of inflatable members being disposed in a location on said stent to be inflatable to abut against a surface, upon said stent being deployed at said deployment site, wherein another medical device extends radially outwardly through said stent and between selected adjacent ones of said plurality of inflatable members such that said plurality of inflatable members upon inflation press against said another medical device.

2. The device according to claim 1, wherein said inflatable members are spaced sufficiently closely to press against each other upon inflation.

3. An intravascular medical device, comprising:
    a stent having a lumen therethrough and having a small dimension for placement into a delivery device for delivery to a deployment site in a vessel of a patient and being expandible thereat to an enlarged dimension, and
    at least one inflatable member secured to said stent, said at least one inflatable member being sufficiently small in a deflated state to be placed into said delivery device for delivery to said deployment site, said at least one inflatable member being disposed in a location on said stent to be inflatable to abut against a surface, upon said stent being deployed at said deployment site, wherein said at least one inflatable member is affixed to said stent along an inner surface thereof to expand radially inwardly upon inflation.

4. An intravascular medical device, comprising:
    a stent having a lumen therethrough and having a small dimension for placement into a delivery device for delivery to a deployment site in a vessel of a patient and being expandible thereat to an enlarged dimension, and
    a plurality of inflatable members secured to said stent and being sufficiently small in a deflated state to be placed into said delivery device for delivery to said deployment site,
    said plurality of inflatable members being disposed in a location on said stent to be inflatable to abut against a surface, upon said stent being deployed at said deployment site, wherein said plurality of inflatable members are affixed to said stent along an inner surface thereof to expand radially inwardly upon inflation.

5. The device according to claim 4, wherein at least two said inflatable members are positioned to face each other within said lumen and to press against each other upon inflation to occlude said lumen.

6. An intravascular medical device, comprising:
    a stent having a lumen therethrough and having a small dimension for placement into a delivery device for delivery to a deployment site in a vessel of a patient and being expandible thereat to an enlarged dimension, and
    at least one inflatable member secured to said stent, said at least one inflatable member being sufficiently small in a deflated state to be placed into said delivery device for delivery to said deployment site,
    said at least one inflatable member being disposed in a location on said stent to be inflatable to abut against a surface, upon said stent being deployed at said deployment site, wherein said stent includes at least one spiral strut and said at least one inflatable member is affixed to said stent along at least one circumference of said spiral strut.

7. The device according to claim 6, wherein said stent includes a plurality of spiral struts with several of said spiral struts having respective said inflatable members affixed thereto.

8. An intravascular medical device, comprising:
    a stent having a lumen therethrough and having a small dimension for placement into a delivery device for delivery to a deployment site in a vessel of a patient and being expandible thereat to an enlarged dimension, and
    at least one inflatable member secured to said stent and being sufficiently small in a deflated state to be placed into said delivery device for delivery to said deployment site,
    said at least one inflatable member being disposed in a location on said stent to be inflatable to abut against a surface, upon said stent being deployed at said deployment site, wherein at least a second stent extends outwardly from an outer surface of said stent to an end that is within a branch vessel upon deployment, and wherein said stent includes a pair of annular ones of inflatable members affixed to said stent along said outer surface thereof on distal and proximal sides of said second stent to seal said stent against said vessel wall distally and proximally of said branch vessel.

9. The device according to claim 8, wherein said second stent includes at least one inflatable member affixed thereto proximate said end of said second stent.

10. The device according to claim 8, wherein a third stent extends outwardly from said outer surface of said stent between said pair of annular ones of inflatable members, to a respective end that is within another branch vessel upon deployment.

11. An intravascular medical device, comprising:
    a stent having a lumen therethrough and having a small dimension for placement into a delivery device for delivery to a deployment site in a vessel of a patient and being expandible thereat to an enlarged dimension, and
    at least one inflatable member secured to said stent and having an inflation lumen extending therefrom, said at least one inflatable member being sufficiently small in a deflated state to be placed into said delivery device for delivery to said deployment site; and
    said at least one member being affixed to an inner surface of said stent to expand radially inwardly upon inflation and engage and press against either itself or another said at least one inflatable member to occlude said lumen of said stent.

* * * * *